US009995674B2

(12) United States Patent
Prasad

(10) Patent No.: US 9,995,674 B2
(45) Date of Patent: Jun. 12, 2018

(54) PHOTOACOUSTIC CHEMICAL DETECTOR

(71) Applicant: The United States of America as represented by the Administrator of the National Aeronautics and Space Administration, Washington, DC (US)

(72) Inventor: Narasimha S. Prasad, Yorktown, VA (US)

(73) Assignee: THE UNITED STATES OF AMERICA AS REPRESENTED BY THE ADMINISTRATOR OF NASA., Washington, DC (US)

( * ) Notice: Subject to any disclaimer, the term of this patent is extended or adjusted under 35 U.S.C. 154(b) by 573 days.

(21) Appl. No.: 14/584,004

(22) Filed: Dec. 29, 2014

(65) Prior Publication Data

US 2018/0095026 A1    Apr. 5, 2018

Related U.S. Application Data

(60) Provisional application No. 61/920,800, filed on Dec. 26, 2013.

(51) Int. Cl.
*G01N 21/17* (2006.01)
*G01N 21/39* (2006.01)
(Continued)

(52) U.S. Cl.
CPC .......... *G01N 21/1702* (2013.01); *G01B 9/02* (2013.01); *G01H 9/006* (2013.01); *G01N 21/39* (2013.01);
(Continued)

(58) Field of Classification Search
CPC .. G01H 9/00; G01B 9/02003; G01B 9/02004; G01D 5/266; G01N 21/1702; G01N 2021/1704; G01N 21/3504
(Continued)

(56) References Cited

U.S. PATENT DOCUMENTS 4,554,836 A    11/1985 Rudd
4,816,125 A *   3/1989 Muller .................. H04R 17/00
                                                      204/192.18
(Continued)

OTHER PUBLICATIONS

Chen-Chia Wang, et al., "Non-Contact Human Cardiac Activity Monitoring Using a High Sensitivity Pulsed Laser Vibrometer," CLEO: Science and Innovations, May 1-6, 2011, pp. 1-2, Baltimore, Maryland.

(Continued)

*Primary Examiner* — Manish S Shah
*Assistant Examiner* — Suman K Nath
(74) *Attorney, Agent, or Firm* — Jonathan B. Soike; Andrea Z. Warmbier; Mark P. Dvorscak

(57) ABSTRACT

A laser vibrometer for measurement of ambient chemical species includes a laser that produces a beam that is split into a reference readout beam and a signal readout beam. A probe laser beam is tuned to an absorption feature of a molecular transition, and generates acoustic signals when incident on a gaseous species via the photo acoustic effect. The scattered acoustic signals are incident on a thin membrane that vibrates. The readout laser beam reflected from the vibrating membrane is mixed with the reference beam at the surface of a photo-EMF detector. Interferrometric fringes are generated at the surface of the photo-EMF detector. Electric current is generated in the photo-EMF detector when the fringes are in motion due to undulations in the signal readout beam imparted by the vibrating membrane. A highly sensitive photo-EMF detector is capable of detecting picoJoules or less laser energy generated by vibrating processes.

16 Claims, 6 Drawing Sheets

(51) Int. Cl.
  *G01N 29/24* (2006.01)
  *G01N 29/46* (2006.01)
  *G01H 9/00* (2006.01)
  *G01B 9/02* (2006.01)
  *G01N 21/3504* (2014.01)
  *G01N 21/31* (2006.01)

(52) U.S. Cl.
  CPC ......... *G01N 29/2418* (2013.01); *G01N 29/46* (2013.01); *G01N 2021/1704* (2013.01); *G01N 2021/1761* (2013.01); *G01N 2021/3125* (2013.01); *G01N 2021/3185* (2013.01)

(58) Field of Classification Search
  USPC .......... 73/24.02, 24.06, 31.01, 31.02, 31.03, 73/61.48, 61.49, 61.79, 64.53, 643, 657; 356/432, 436, 437, 451, 484, 486, 487, 356/502
  See application file for complete search history.

(56) References Cited

U.S. PATENT DOCUMENTS

| | | | | |
|---|---|---|---|---|
| 4,956,538 | A * | 9/1990 | Moslehi | G01J 5/0003 219/121.6 |
| 5,883,715 | A | 3/1999 | Steinlechner et al. | |
| 6,202,470 | B1 * | 3/2001 | Chou | G01N 21/1702 250/339.13 |
| 6,477,189 | B1 * | 11/2002 | Takeda | H01S 5/0687 372/32 |
| 6,600,564 | B1 | 7/2003 | Wang et al. | |
| 8,072,609 | B1 | 12/2011 | Trivedi et al. | |
| 2004/0094716 | A1 * | 5/2004 | Evan Webber | G01N 21/1702 250/339.12 |
| 2007/0115475 | A1 * | 5/2007 | Shpantzer | G01N 21/171 356/451 |
| 2012/0153119 | A1 * | 6/2012 | Patil | B82Y 30/00 250/200 |
| 2013/0205871 | A1 * | 8/2013 | Zeninari | G01N 21/1702 73/24.02 |
| 2014/0084395 | A1 * | 3/2014 | Sparks | G01L 9/008 257/416 |

OTHER PUBLICATIONS

Chen-Chia Wang, et al., "A New Kind of Laser Microphone Using High Sensitivity Pulsed Laser Vibrometer," CLEO, Quantum Electronics and Laser Science Conference, May 4-9, 2006, pp. 1-2, San Jose, California.

Chen-Chia Wang, et al., "Biological Life Signs Detection Using High Sensitivity Pulsed Laser Vibrometer," Conference on Lasers and Electro-Optics (CLEO), May 6, 2007, pp. 1-2, Baltimore. Maryland.

Chen-Chia Wang, et al., "Human Life Signs Detection Using, High-Sensitivity Pulsed Laser Vibrometer," IEEE Sensors Journal, 2007, pp. 1-7, vol. 7, No. 9.

Chen-Chia Wang, et al., "Non-Contact Cardiac Activity Monitoring Using Pulsed Laser Vibrometer," Sensors & Transducers, Received Nov. 12, 2013, Published Jan. 31, 2014, pp. 173-176, vol. 162, IFSA Publishing, S.L.

* cited by examiner

PHOTOACOUSTIC CHEMICAL DETECTOR

CROSS-REFERENCE TO RELATED PATENT APPLICATION

This patent application claims the benefit of and priority to U.S. Provisional Patent Application No. 61/920,800, titled "PHOTO-ACOUSTICS SENSING BASED LASER VIBROMETER FOR THE MEASUREMENT OF AMBIENT CHEMICAL SPECIES" filed on Dec. 26, 2013, the contents of which are hereby incorporated by reference in their entirety.

STATEMENT REGARDING FEDERALLY SPONSORED RESEARCH OR DEVELOPMENT

The invention described herein was made by an employee of the United States Government and may be manufactured and used by or for the Government of the United States of America for governmental purposes without the payment of any royalties thereon or therefore.

BACKGROUND OF THE INVENTION

Vibrometer technology involves the detection and analysis of pressure waves, such as acoustic waves or water waves, that might bear information regarding agitation sources of interest to the observer. Conventional microphones are capable of detecting such waves with varying degrees of accuracy and resolution satisfactory for general applications. Microphone-like devices and technologies possess a pressure-sensing interface, including but not limited to, a diaphragm that receives the incoming acoustic pressure waves and conform its physical motion to mimic that of the incident acoustic, i.e., pressure, waves. In conventional microphones, additional mechanical parts are in general connected to the diaphragm so as to convert the motion of the diaphragm into signals of electrical nature that allow further processing and applications. Such auxiliary mechanical parts might include an electrically conducting rod to induce alternating electrical currents that approximate the motion of the diaphragm, and hence the incoming pressure waves, or alternatively, to induce a capacitance which subsequently leads to a measurable electrical current. Unfortunately, such auxiliary mechanical parts add significant weight to the assembly, and alter/limit the resultant frequency response towards the lower end. Furthermore, such added weight also negatively impacts the sensitivity of the diaphragm assembly in detecting the incoming pressure waves, e.g., acoustic waves, due to the fact that such mechanical parts have innate inertia which can only be overcome by larger amplitude pressure waves, to move and generate detectable output signals.

A more modern alternative, as disclosed in U.S. Pat. Nos. 4,554,836 and 5,883,715, involves use of laser vibrometers, i.e. optical microphone technology that does not require auxiliary mechanical components. Instead, a beam of light, such as a laser, is split into two parts, one which forms a reference beam and the second which forms a sensing beam which impacts the target surface, e.g., the pressure-sensing diaphragm, and is reflected therefrom, the sensing beam. The sensing beam is homodyned with the reference beam to produce a phase modulated signal, an interference pattern. This interference pattern models the surface displacement of the target surface, is converted via, an optical interferometer, i.e., a Michelson interferometer, and photodetectors, i.e., photodiodes, to generate a usable, alternating electric current, which mimics the motion/vibration of the target surface, i.e., the pressure-sensing diaphragm.

A known refinement on the laser vibrometer involves using optical grating-like devices consisting of a structure of interdigitated fingers constructed with semiconductors using processes similar to MicroElectroMechanical Systems (MEMS) technology. Instead of using optical interferometers and photodiodes to determine the diaphragm movement, an optical beam is shone onto the semiconductor MEMS like structure while the back-diffracted light beam intensity is monitored. Movements of the interdigitated fingers cause the back-diffracted light beam intensity to exhibit similar temporal changes and thus by monitoring the diffracted light beam intensity, interpretation of the diaphragm movement can be obtained.

In some state-of-the-art optical microphones, an optical fiber probe is deployed with a pressure-sensing diaphragm attached to the tip thereof. The probe light is projected onto the sensing interface and the back-reflected light is collected by the optical fiber tip and sent to the optical interferometer for signal retrieval. In such approaches, the detection sensitivity is very limited due in part to the fact that the aperture of optical fiber is generally very limited, especially for the single-mode fiber that is needed for the said fiber-optic microphones to avoid the generation of higher order modes that would diminish the detected signal output. As a result, the probe light beam must be projected onto the pressure-sensing interface within a very tight angle from normal incidence. This means that the probe light beam can only interrogate the pressure-sensing interface once and hence no possibility of further boosting up the detected signal strength.

Frequently, the detection, resolution and analysis of pressure waves from very weak acoustic signals are required, such as detection of molecules emitted from certain explosives and detection of submerged submarines. In general, optical microphones suffer from limited sensitivity and scalability of output which limits their applicability to analysis of such weak signals. This limited sensitivity results from use of optical interferometers for the detection mechanism, wherein the wavelength of the light beam involved is used as a gauge to monitor the scale of movement of the pressure-sensing diaphragm. Because the optical light sources have a wavelength of approximately 1 micrometer, it becomes increasingly difficult to detect diaphragm movements in scales smaller than 1 nanometer ($10^{-9}$ meter). Further, with weak signals and longer standoff distances, i.e., the distance between the source and sensing interface or diaphragm, it may become necessary to detect diaphragm movements in the order of 1 picometer ($10^{-12}$ meter). In fact, for the above examples, involving very weak pressure waves, at distances in the tens of meters away from the diaphragm, it is necessary to detect vibrations of the diaphragm even less than 1 picometer ($10^{-12}$ meter).

Another alternative, as described in U.S. Pat. No. 8,072,609 involves a vibrometer that uses either a continuous-wave or pulsed laser source to generate a reference beam and a sensing beam. The sensing beam is bounced at least once, preferably twice, or most preferably multiple times, against a pressure-wave sensing diaphragm, using a reflective mirror assembly that is sized and curved to enhance the signal strength being captured by the sensing beam, in terms of power spectral density, and to enhance the resolution of the vibration being captured by the sending beam. The signal strength is enhanced as a function of the number of bounces squared and the resolution is enhanced down to an experimentally demonstrated displacement of the pressure-wave sensing diaphragm of approximately 4 picometers. The process involves splitting the laser emission into two parts or branches, the first part being the reference beam which is projected onto a photosensor directly. The second part or branch is the sensing beam, which is repeatedly bounced off a mirror onto the pressure-wave sensing diaphragm, or interface, before being sent to the photosensor for comparison with the reference beam. The vibrometer may use standard laser vibrometer interference technology, disclosed in U.S. Pat. Nos. 4,554,836 and 5,883,715. Another approach for the comparison is the adoption of photo-electromotive force (photo-EMF) sensors as disclosed in U.S. Pat. No. 6,600,564. This photosensor is capable of detecting the temporal phase variations between the reference and sensing light beams by generating photo currents which mimic those of the phase variations between the light beams and therefore the vibrations of the diaphragm's surface.

BRIEF SUMMARY OF THE INVENTION

One aspect of the present invention is a laser vibrometer capable of detecting and displaying pressure waves from acoustic signals that are generated by a chemical species via photoacoustic effect due to its excitation by a laser whose wavelength coincides with an absorption feature. The laser vibrometer comprises a laser configured to produce a beam of monochromatic light, and a beam splitter that is configured to split the beam of monochromatic light into a reference beam and a sensing beam. The reference beam is directed to a photosensor. The laser vibrometer also includes a pressure-sensing diaphragm having a first side which when impacted by the pressure waves responsively vibrates, and a second side having a mirror-like surface finish. The sensing beam is directed against the second side of the pressure sensing diagram. The sensing beam may be reflected therefrom to an optional reflective mirror assembly. The mirror assembly is configured to reflect the sensing beam back against the pressure sensing diaphragm. The sensing beam is then directed to the photosensor. The photosensor is a photo-EMF sensor, which homodynes the sensing beam with the reference beam to output an analog signal whose phase modulation is proportional to the displacement of the diaphragm caused by the incident pressure wave. A displacement of the diaphragm as small as about 10 femtometers or less can be detected. The laser vibrometer may include a display that is configured to display the analog signal.

The present invention includes several laser vibrometer configurations. The laser in the laser vibrometer section may be referred to as a reference laser or a baseline laser. The purpose of the reference laser is to detect vibrations. The purpose of the second laser, known as the probe laser, is to excite the chemical species by matching its wavelength with its absorption feature to generate sound waves comprising a photoacoustic signature. A laser vibrometer for chemical detection according to the present invention includes a probe laser having a wavelength corresponding to the absorption feature of a given chemical species. The probe wavelength can be generated either by a separate probe laser or the baseline laser. For the detection of a specific chemical species, the probe laser preferably has a single longitudinal mode for efficient detection of given chemical species and for concentration estimation (i.e. estimating the concentration of the specific chemical species that is detected).

In a laser vibrometer according to one aspect of the present invention, two lasers, namely the reference (baseline) and probe lasers, are utilized and the chemical species that is to be detected is disposed external to the vibrometer. Any suitable laser wavelength may be used for the baseline laser to obtain maximum vibration sensitivity. A second laser (probe laser), is external to the baseline vibrometer setup. The wavelength of the probe laser is selected to match an absorption feature of the specific chemical species to be detected whereby sound waves comprising an acoustic signature are generated if the probe laser interacts with the specific chemical species to be detected (i.e. if the chemical species is present). The generated acoustic signature is then allowed to be incident on a sensitive diaphragm to generate vibrations. The interference of signal and reference laser beams are directed to a photo-EMF detector, and the beams generate photocurrent by on/in the photo-EMF detector. The laser vibrometer may include succeeding transimpedance amplifier and post processing electronics that provide for amplification and filtering.

A laser vibrometer according to another aspect of the present invention utilizes a reference laser that also acts as a probe laser for the detection of chemical species that are present outside the vibrometer. In this case, the reference laser wavelength matches with an absorption feature and the reference laser beam is directed to propagate through a region of interest to obtain a photoacoustic signature.

In a vibrometer according to another aspect of the present invention, the chemical species is present inside the vibrometer and one arm of the reference laser beam propagates through the chemical species and generates a photoacoustic signature that is accordingly detected. In this case, the reference laser is the probe laser. The chemical species may be made available inside the device through an inlet (forced or self-spreading).

A laser vibrometer according to the present invention may also be utilized for wavelength calibration for laser-based chemical detection LIDAR systems. No additional lasers are required for this application because the test laser beam is provided by the LIDAR system. The vibrometer is hermetically sealed with a known quantity of a given chemical species and suitably calibrated. When the test beam is incident on this vibrometer, the generated signal strength is used to determine the extent of the test laser beam coincidence with the absorption feature. Based on the vibration signal strength, the laser wavelength of the LIDAR system can be tuned to optimize its performance.

Another aspect of the present invention is a photo-EMF sensor/detector having enhanced absorption sensitivity and spectral range. The sensitivity and spectral range may be enhanced by tuning the bandgap of the photo-EMF detector material to the laser vibrometer transmitter wavelengths which are selected based on the absorption feature of the chemical species to be detected. In order to enhance the spectral sensitivity and spectral range, two approaches may be utilized. In the first, multiple doping of transition elements into CdSe or similar photo-EMF detector material host matrix is utilized. In the second, nanotechnology based bandgap tuned photo-EMF detector material is utilized. Here, using nanoprocessing techniques, nanoparticles of photo-EMF detector material such as CdSe, arranged in various ranges of sizes, enables bandgap tuning. Bandgap tuning expands the detector's spectral range. These two approaches can be used independently or simultaneously for the fabrication of advanced photo-EMF detectors. However, simultaneous use of both may provide better performance.

Another aspect of the present invention is an improved diaphragm. In order to respond to tiny vibrations generated by impinging photoacoustic signatures, the diaphragm in the interferometer segment must be highly sensitive. Detection of displacements in the order of Picometer and Femtometer levels or less significantly benefit ambient chemical detection. A diaphragm according to the present invention may have a membrane that comprises ZnO nanolayered on Silicon (Si) or ZnO that is nanolayered on Silicon Carbide (SiC). These membranes provide significantly improved sensitivity to photoacoustic vibrations.

These and other features, advantages, and objects of the present invention will be further understood and appreciated by those skilled in the art by reference to the following specification, claims, and appended drawings.

DETAILED DESCRIPTION OF THE INVENTION

Figure 1:
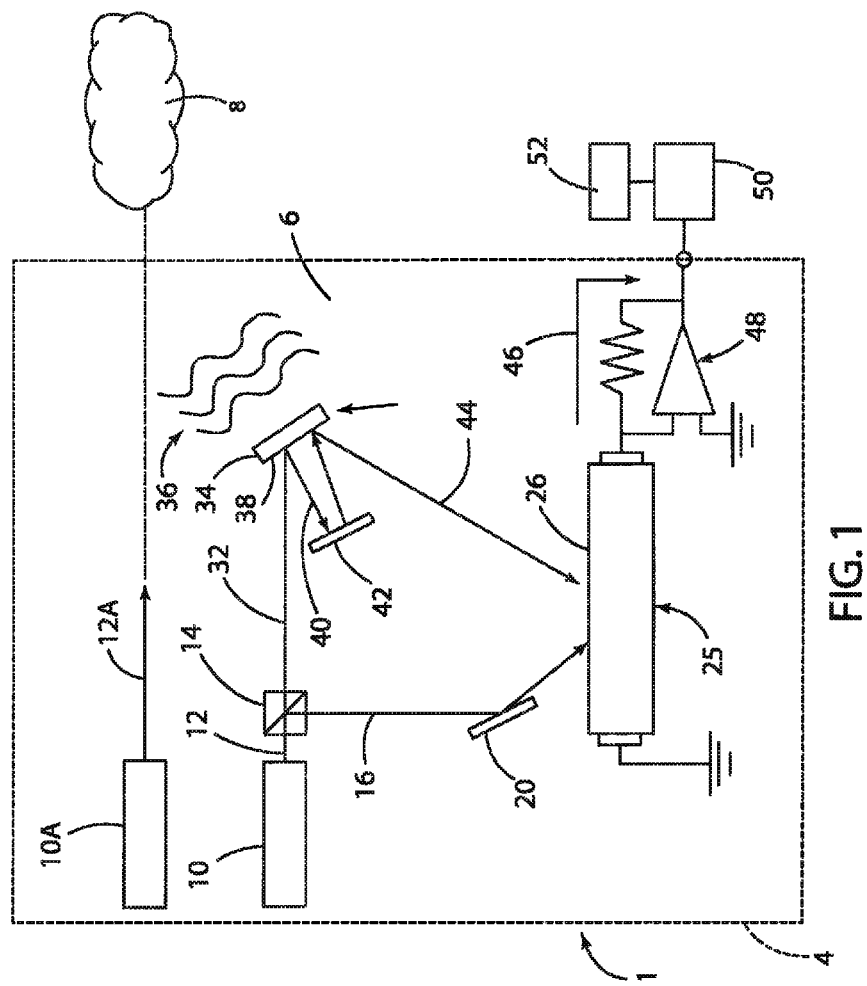
FIG. 1 depicts a laser vibrometer according to one aspect of the present invention.

For purposes of description herein, the terms "upper," "lower," "right," "left," "rear," "front," "vertical," "horizontal," and derivatives thereof shall relate to the invention as oriented in FIG. 1. However, it is to be understood that the invention may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

With reference to FIG. 1, a laser vibrometer 1 according to one aspect of the present invention includes a light source such as a laser 10. Laser 10 can be either a continuous or a pulsed laser, preferably a pulsed laser, which may be either a conventional modestly average-powered, Q-switched and mode-locked laser, such as, a neodymium-doped yttrium aluminum garnet laser (Nd:YAG), which emits a light beam 12. The emitted light beam 12 is then split into two branches by a standard beam splitting element 14. The reference light beam 16, newly split from beam 12, is directed via a mirror 20 to a photo-EMF sensor 25. As discussed in more detail below, photo-EMF sensor 25 is preferably configured to provide enhanced absorption sensitivity and spectral range.

The sensing light beam 32 is directed onto a diaphragm 34, whose motion is being affected and controlled by the incident pressure waves 36, the acoustic signature of interest produced as a result of interaction of sensing light beam 32 and chemical species 8. The pressure-sensing diaphragm 34 has a mirror-like surface finish on at least the face 38 where the sensing beam 32 impinges thereon, to minimize any reflection and scattering optical losses that might be suffered by the reflected light beam 40. The initial reflected sensing light beam 40 may be re-directed by an optional reflective mirror assembly 42 back onto the pressure-sensing diaphragm 34 a set number of times by appropriately sizing and curving the reflective mirror assembly to enhance the measurement of the acoustic signature of pressure waves 36. While only two bounces are made by the probe light beam onto the pressure-sensing diaphragm in the embodiment shown in FIG. 1, it is to be understood that the total number of bounces can be more or less than 2, with the upper bound number being determined by the loss characteristics of the system/components involved, the distance between the diaphragm element 34 and the reflective mirror assembly 42, the power level of laser 10, and in the case of the shown pulsed light source, the laser pulse width.

The final sensing beam 44, upon completion of the desired number of bounces, exits the diaphragm mirror assembly. The final sensing beam 44 is directed onto the photo-EMF sensor 25, which heterodynes this final sensing beam 44 with the reference beam 16 to output an analog signal whose phase modulation is proportional to the displacement of the diaphragm 34 caused by the incident pressure wave 36. This analog signal is the photocurrent signal 46 that can be converted into voltage signal using a transimpedance amplifier 48, which voltage signal is displayed or sent to a digital computer 50 for analysis and reporting via a display screen 52.

The photocurrent signal 46 generated by the photo-EMF sensor 25 can be expressed approximately as:

$$j^\Omega(t) = \kappa \varphi(t) \times P_{probe}(t) \quad (1)$$

where $P_{probe}(t)$ is the back-scattered sensing light beam power density impinging onto the photo-EMF sensor 25 and κ is a constant determined by the geometric arrangement of the light beams, sensor material characteristics, photon energy, as well as the reference light beam intensity. Herein φ(t) represents the total amount of phase modulation imposed onto the sensing light beam 32 by the pressure-sensing diaphragm 34. Equation (1) shows that stronger signal photocurrents are generated when the amount of phase modulation is increased or a higher optical power density of the sensor light beam is available. The output signal strength and its detection sensitivity may be increased by using a multi-bounce arrangement as described in U.S. Pat. No. 8,072,609 as well as the deployment of a pulsed light source, including but not limited to, Q-switched and mode-locked lasers where the laser energy is concentrated within short time periods to produce transiently very high peak optical power density levels while maintaining modest optical power density level averaged over time. However, it will be understood that the present invention is not limited to a multi-bounce arrangement, and the reflective mirror assembly 42 is therefore optional.

Considering the presence of a temporal pressure wave of sinusoidal nature and that, upon its interaction with the pressure-sensing diaphragm 34, causes the pressure-sensing diaphragm 34 to conform and exhibit surface vibrations that can be described mathematically as:

$$d \sin(\omega t) \quad (2)$$

where ω is the angular frequency of the vibration as well as that of the impinging pressure wave 36 and d is the maximal displacement of the pressure-sensing diaphragm 34 under the effects of the impinging pressure wave 36. A conversion relationship exists between the strength of the impinging pressure wave 36 and the resultant surface displacement by the sensing diaphragm 34. This relationship is determined by the design, dimensions, and the characteristics of the materials forming the pressure-sensing diaphragm 34. The amount of phase modulation imposed onto the sensing light beam 32 upon its one bounce from the pressure-sensing diaphragm 34 is given by:

$$4\pi d \sin(\omega t)/\lambda \quad (3)$$

where λ is the wavelength of the light beam. By repeatedly bouncing the sensing light beam 32 onto the diaphragm 34, as shown schematically in FIG. 1, it can be shown that the total amount of phase modulation suffered by the sensing light beam 32 upon its final exit from the pressure-sensing diaphragm 34, as the final sensing beam 44, and reflective mirror assembly 42 is given by:

$$\varphi(t) = \Sigma_n d \sin[\omega t + (n-1)\varphi_0] \times 4\pi/\lambda \quad (4)$$

where n=1, 2 . . . N, with N representing the total number of bounces the sensing beam strikes the pressure-sensing diaphragm. The static phase $\varphi_0 = \omega \times 2$ L/c, where L is the separation between the pressure-sensing diaphragm 34 and the reflective mirror assembly 42 and c is the speed of light, is the additional phase delay experienced by the sensing light beam 32 upon its round-trip passage between the pressure-sensing diaphragm 34 and the reflective mirror assembly 42. It can be seen readily from Equation (4) that if the additional phase shift $N \times \varphi_0$ is negligible due to, for example, the limited number of bounces or minimal separation between the pressure-sensing diaphragm 34 and the reflective mirror assembly 42 (i.e., N×2 L<<the spatial extent of the laser pulses), the total phase modulation suffered by the probe light beam can then be approximated by:

$$\varphi(t) \approx N \times d \sin(\omega t) \times 4\pi/\lambda \quad (5)$$

which is greater than the phase modulation imposed by the single-bounce embodiment, Equation (3), by a factor of N. Thus, under these conditions, the vibration amplitude of sensing diaphragm caused by the incident pressure waves can be effectively amplified by multi-bounce arrangements which proportionally enhance the resultant output signal strength, as clearly indicated by Equation (1). Indeed, the enhancement in the detected output signal strength expressed in power spectral density is given by $N^2$. Thus by increasing the number of total bounces, N, the detected output signal strength caused by the impinging pressure waves can be increased.

The laser vibrometer 1 may optionally include a second laser 10A that produces a second beam of light 12A that is incident on chemical species 8. The wave length of light 12A is selected on the basis of a desired molecular transition or an absorption feature of a molecule of interest to generate acoustic signatures 36 via the photo-acoustic effect. If a second laser 10A is utilized, the beam of light 12A comprises a probe beam. The lasers 10 and 10A may be mounted in a housing 4 having one or more openings (not shown) that permit entry of gas and other substances comprising chemical species 8 into the interior space 6 of the housing 4 to permit use of sensing light beam 32 as a probe. The housing 4 may comprise a compact, hand-held module that may be utilized for in-situ and short distance measurements. The laser vibrometer 1 may also be extended for use at longer ranges by energy scaling the probe laser 10A and by efficiently collecting the acoustic signals generated from desired chemical species. Alternatively, the probe beam 12A from laser 10A may be directed to a remote location outside of the housing 4 to produce pressure waves 36 that are then transmitted into the interior space 6 of housing 4 through openings (not shown) in housing 4.

The lasers 10 and/or 10A may comprise solid-state lasers, semi-conductor lasers, or quantum cascade lasers. Furthermore, the interferometric setup can be either direct or coherent type. As discussed above, the coherent technique allows sensitive phase measurements via heterodyning that is achieved by frequency shifting of the reference beam 16 to improve concentration resolution.

The probe laser wavelength is preferably a single longitudinal mode. It is preferably pulsed or intensity modulated to obtain substantial photoacoustic signatures. The probe laser beam may be focused using a lens to increase the magnitude and range. The probe laser wavelengths can be derived from any nonlinear processes including from a tunable solid state laser, a semiconductor laser, an optical parametric oscillator providing tunable laser wavelengths, a quantum cascade semiconductor laser, oan optical parametric oscillator providing tunable laser wavelengths, or a quantum cascade laser.

Laser vibrometers according to the present invention permit sub-ppb and below measurements to be achieved. The laser virbometers can be used to sense and measure any of the atmospheric trace gasses and traces of chemical species including toxic agents such as those present in TEDs, nerve gas, etc.

According to one example, laser vibrometer 1 may be configured to sense ambient $CO_2$ utilizing a probe laser operating at 1.571 micron spectral band. If a single laser 10 is utilized, the sensing light beam 32 comprises a probe beam. Alternatively, if a second laser 10A is utilized, the beam 12A comprises a probe beam. The laser radiation is tuned to the center of a strong transition in this spectral band and therefore generates acoustic signals 36 if $CO_2$ is present in the gaseous medium through which the probe beam passes. As discussed above, the readout laser beam 32 reflects from the membrane 34 and carries intensity undulations due to vibrations of the diaphragm 34 and therefore generates moving fringes on surface 26 of photo-EMF detector 25. The magnitude of the photo-EMF current corresponding to the minute acoustic vibrations of the membrane 34 may be calibrated for the laser specifications, range, and probe volume of chemical species to thereby provide concentration information of the gaseous species of interest.

Diaphragm 34 may comprise a silicon carbide membrane that is several microns thick. To response to tiny vibrations generated by impinging photoacoustic signatures, the diaphragm 34 has to be highly sensitive. Diaphragm 34 is preferably capable of detecting displacements in the order of Picometer and Femtometer levels or less. This significantly benefits ambient chemical detection. Diaphragm 34 may comprise a membrane including ZnO that is nanolayered on Silicon (Si) or Silicon Carbide (SiC). Diaphragms fabricated using ZnO nanostructures on Si or SiC membranes provide enhanced response for impinging photoacoustic vibrations. ZnO has a relatively large direct bandgap energy and exhibits long lifetimes of optical phonons that facilitates vibration sensing.

Absorption sensitivity and spectral range can be enhanced by tuning the bandgap of the photo-EMF detector material of photo-EMF detector 25 to the laser vibrometer transmitter wavelengths which are selected based on the absorption feature of specific chemicals to be detected. In order to enhance the spectral sensitivity and spectral range, two techniques may be used. In the first case, multiple doping of transition elements into CdSe or similar photo-EMF detector material host matrix is utilized. In the second case, a nanotechnology based bandgap tuned photo-EMF detector 25 is utilized. Using nanoprocessing techniques, nanoparticles of photo-EMF detector material such as CdSe, arranged in various ranges of sizes enables bandgap tuning. Bandgap tuning expands the detector's spectral range. These two techniques can be used independently or simultaneously for the fabrication of advanced photo-EMF detectors 25. However, simultaneous use of both techniques may provide better performance. The field-of-view, and hence the detection sensitivity, may be enhanced by encapsulating the photo-EMF detector surface 26 in a spatially matched and integrated lens (not shown) of appropriate refractive index that provides maximum transmission to reference wavelength.

Figure 2:
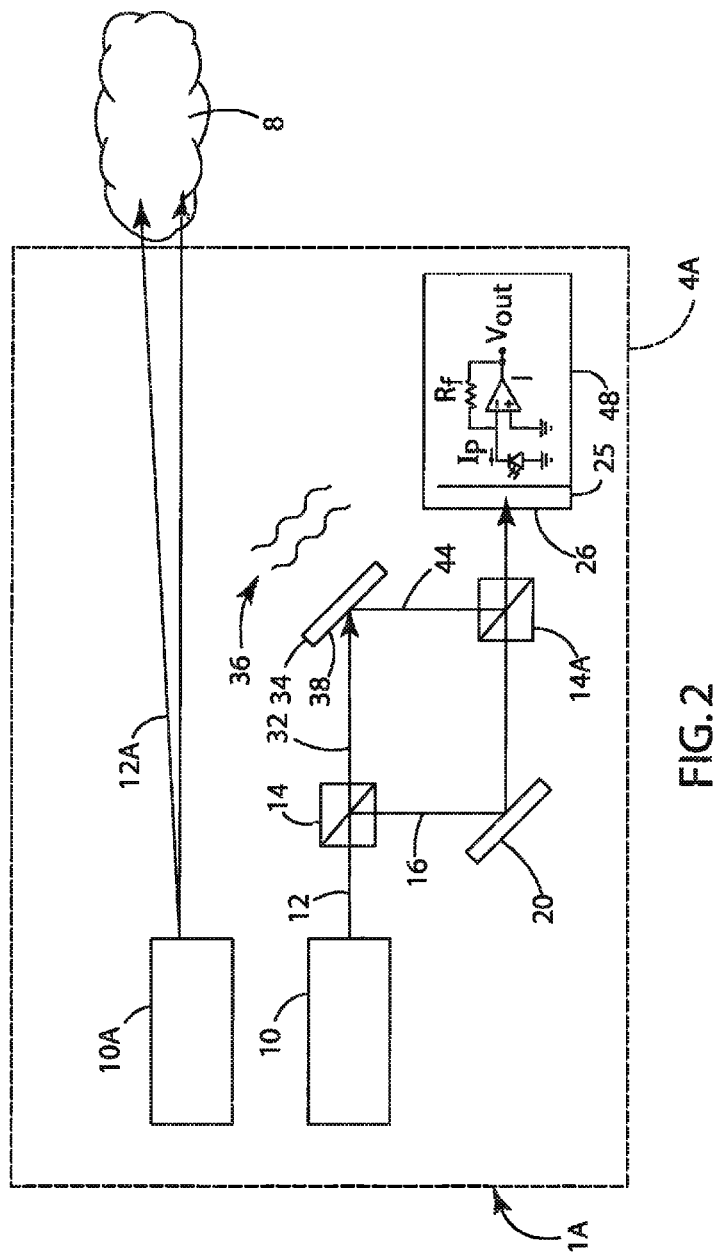
FIG. 2 depicts a laser vibrometer according to another aspect of the present invention.

With reference to FIG. 2, a laser vibrometer 1A according to another aspect of the present invention includes a reference laser 10 and a probe laser 10A. The vibrometer 1A includes a second beam splitter 14A that combines the reference light beam 16 and final sensing beam 44 and directs the resulting beam onto surface 26 of photo-EMF sensor 25. Vibrometer 1A does not include a reflective mirror assembly 42 as shown in the laser vibrometer 1 of FIG. 1. The laser vibrometer 1A may include a support structure such as housing 4A having openings or the like (not specifically shown) that permit the light beams 12A to propagate outside of the housing 4A to detect chemical species 8 disposed outside of laser vibrometer 1A. If vibrometer 1A includes a housing, openings (not shown) in the housing permit sound waves 36 to travel from the chemical species 8 to the diaphragm 34. The wavelength of light beam 12A produced by laser 10A is selected to correspond to an absorption feature of a specific chemical species to be detected. Beam 12 produced by laser 10 may have virtually any suitable wavelength of light that is compatible with the photo-EMF detector 25 and related components.

Figure 3:
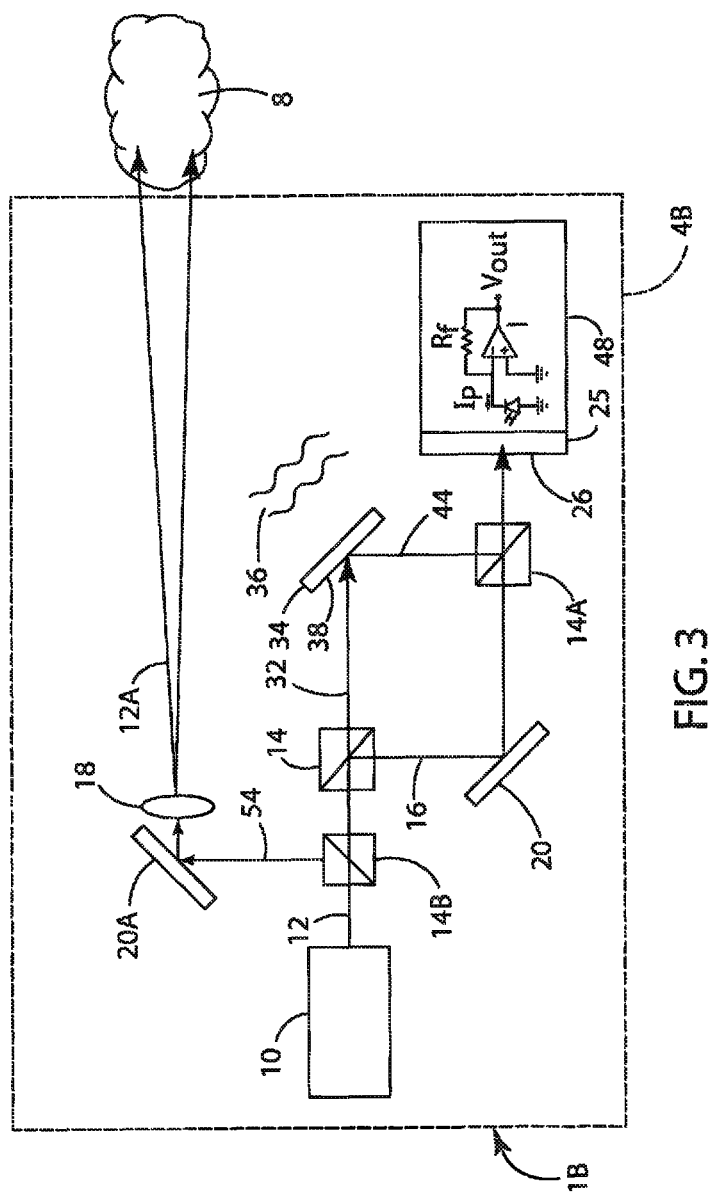
FIG. 3 depicts a laser vibrometer according to another aspect of the present invention.

With further reference to FIG. 3, a laser vibrometer 1B according to another aspect of the present invention includes a beam splitter 14B positioned between laser 10 and beam splitter 14. The beam splitter 14B produces an external sensing or probe beam 54 that is reflected by a mirror 20A. The external beam 54 is then focused/directed by a lens 18 to form second beam of light 12A that is directed towards the chemical species 8. Laser 10 is selected to provide a wavelength of light corresponding to an absorption feature of a specific chemical species to be detected.

Figure 4:
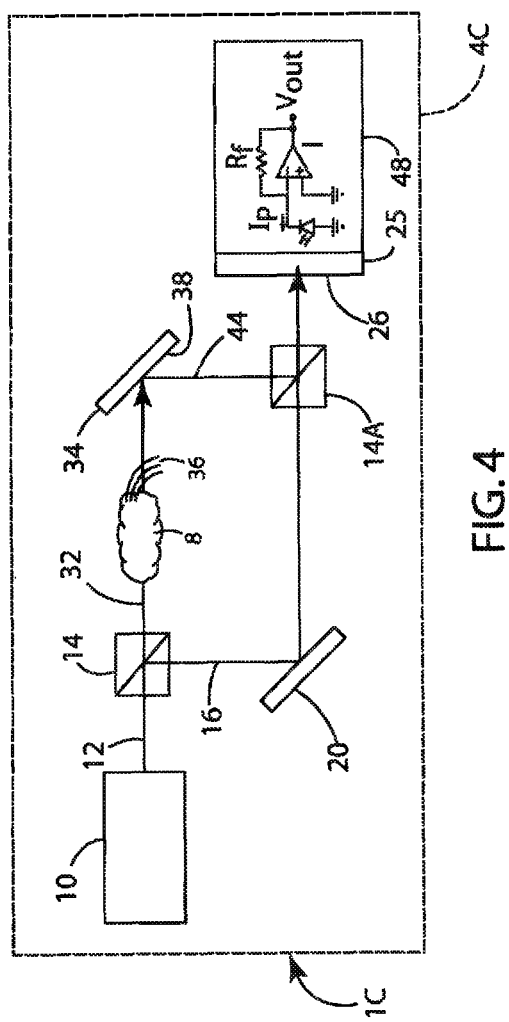
FIG. 4 depicts a laser vibrometer according to another aspect of the present invention.

With further reference to FIG. 4, a laser vibrometer 1C according to another aspect of the present invention includes a probe/reference laser 10 that produces a light beam 12 that is split into a reference light beam 16 and a sensing light beam 32. The laser vibrometer 1C includes a housing 4C having openings (not specifically shown) whereby the chemical species 8 to be detected can enter the housing 4C. The sensing light beam 32 passes through the chemical species 8 and produces pressure waves 36 that are reflected by diaphragm 34. A second beam splitter 14A combines the reference light beam 16 and sensing light beam 32 and directs the resulting beam onto surface 26 of photo-EMF sensor 25. The photo-EMF sensor 25 is preferably configured to detect extremely small changes in sensing light beam 32 due to movement of diaphragm 34. The wavelength of light beam 12 is preferably selected to correspond to an absorption feature of a chemical species 8 that is to be detected.

It will be understood that the beam combiner 14A is optional in the configurations of FIGS. 2-4 because moving fringes can be formed on the surface 26 of the photo-EMF detector 25 itself.

Figure 5:
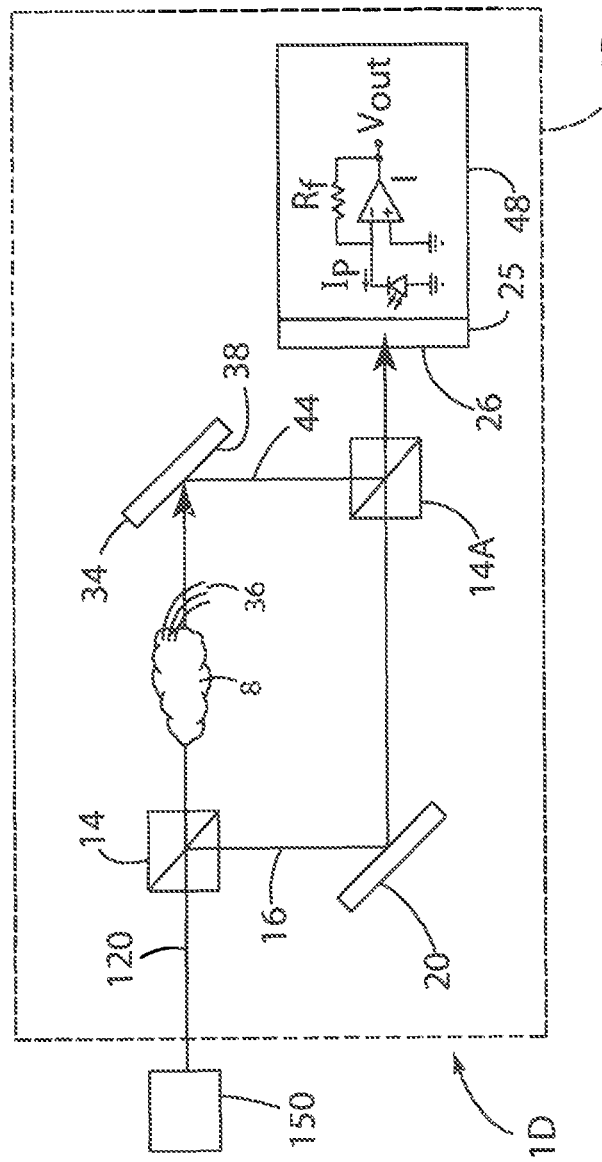
FIG. 5 depicts a laser vibrometer configured for wavelength calibration.

With further reference to FIG. 5, a laser vibrometer 1D according to another aspect of the present invention is configured for wavelength calibration. The laser vibrometer 1D does not include a "dedicated" laser, but rather utilizes a laser beam 120 that is generated by a chemical detection LIDAR system 150. The chemical detection LIDAR system 150 may comprise a known LIDAR system. The laser vibrometer 1D includes a housing 4D or other suitable structure that is hermitically sealed with a known quantity of a given chemical species 8. When the test beam is incident on this device, the generated signal strength may be utilized to determine the extent of the test laser beam 120 that is coincident with the absorption feature of the chemical species 8. Based on the vibration signal strength, the laser wavelength of the LIDAR system 150 can be tuned to optimize its performance.

Figure 6:
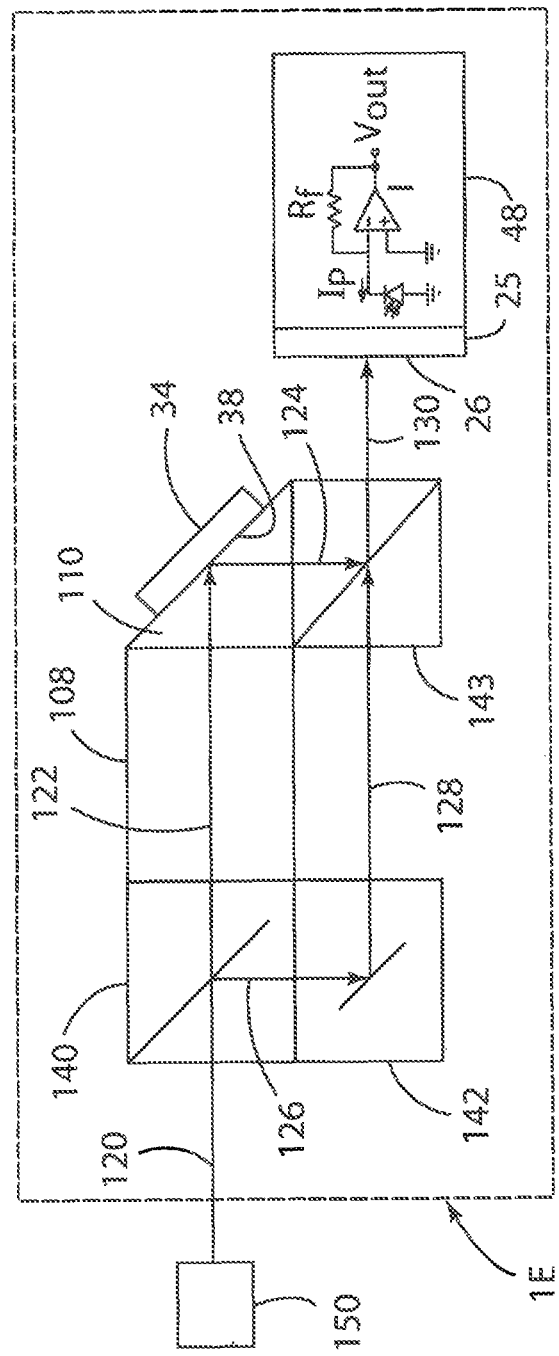
FIG. 6 depicts a laser vibrometer configured for wavelength calibration according to another aspect of the present invention.

With further reference to FIG. 6, a laser vibrometer 1E for wavelength calibration according to another aspect of the present invention includes a first beam splitter 140 (typically 50:50), a total reflector such as a mirror 142, and a beam splitter/combiner 143. A diaphragm 34 is attached to a prism 110 with AR coating at laser wavelength. A gas compartment or cell 108 is filled with a known gas of a specific concentration.

In use, a laser beam 120 from a LIDAR system 150 is initially split into a sensing light beam 122 that passes through the chemical species in the gas cell 108, and a reference light beam 126 that is reflected by the mirror 142 to form beam 128 prior to being recombined by the beam combiner 143 whereby the combined beam 130 is incident on surface 26 of photo-EMF detector 25. The configurations shown for wavelength calibration (FIGS. 5-6) may be used in a feedback loop to automatically tune the test wavelength to the maximum absorption feature of a given chemical species.

The probe laser may have one of the following wavelengths corresponding to a the listed chemical species:
Carbon Di Oxide=1.571, 2.06, and 1.6 microns
Methane=1.65 and 3.3 microns
Oxygen=0.765 and 1.26 microns
Carbon Monoxide=2.34 microns
Ozone=2.91 and 3.08 microns
Nerve gas (Sarin)=9.35 microns
RDX=7.6 microns
Sulphur Di Oxide=300 nm
Nitrous Oxide=448 nm It will be understood that the wavelength of the probe laser of the present invention is not limited to these specific examples.

It will also be understood that the sensor devices of the present invention may be used for photoacoustic imaging for profiling inhomogeneities in test samples. The same devices may also be used for estimating/monitoring stored energies in a photochemical reaction including photosynthesis processes in various environments.

What is claimed is:
1. A laser vibrometer capable of detecting chemical species, comprising:
a light source configured to produce beams of monochromatic light including:
an external probe beam, having a wavelength corresponding to an absorption feature of the chemical species to be detected;

a reference beam; and
a sensing beam;
a pressure-sensing diaphragm which when impacted by the pressure waves resulting from the external probe beam interacting with a chemical species that is located away from the sensing beam responsively vibrates;
a photo-electromotive force (photo-EMF) sensor;
wherein the sensing beam is directed against the second side of the pressure sensing diaphragm; and
wherein the sensing beam is directed to the photo-EMF sensor from the pressure-sensing diaphragm which photo-EMF sensor outputs a signal corresponding to the displacement of the diaphragm caused by the incident pressure wave.

2. The laser vibrometer of claim 1, wherein the light source includes:
a laser configured to produce a beam of monochromatic light having a wavelength corresponding to an absorption feature of the chemical species to be detected;
a first beam splitter configured to split the beam of monochromatic light into the external probe beam and an internal beam; and
a second beam splitter configured to split the internal beam into the reference beam and the sensing beam, the reference beam being directed to a photosensor.

3. The laser vibrometer of claim 2, including:
an external mirror configured to reflect the external probe beam.

4. The laser vibrometer of claim 3, including:
a lens configured to direct the external probe beam after the external probe beam reflects from the external mirror.

5. The laser vibrometer of claim 1, wherein
the laser produces a beam of light having a wavelength of about 2.3 microns to detect carbon monoxide.

6. The laser vibrometer of claim 1, wherein:
the laser produces a beam of light having a wavelength of 1.6 or 3.3 microns to detect methane.

7. The laser vibrometer of claim 1, wherein:
the laser comprises a nonlinear device configured to generate tunable laser wavelengths.

8. The laser vibrometer of claim 1, including:
a housing defining an interior space, and wherein the light source, the pressure-sensing diaphragm, and the photo-EMF sensor are disposed in the interior space.

9. The laser vibrometer of claim 8, wherein:
the external probe beam travels outside of the housing.

10. The laser vibrometer of claim 1, wherein:
the pressure-sensing diaphragm comprises ZnO that is nanolayered onto a silicon-based layer of material.

11. The laser vibrometer of claim 10, wherein:
the silicon-based layer of material comprises a silicon carbide.

12. The laser vibrometer of claim 1, wherein:
the photo-EMF sensor comprises detector material defining a bandgap that is tuned based on the absorption features of a chemical species that is to be detected.

13. The laser vibrometer of claim 12, wherein:
the detector material comprises CdSe having multiple doping of transition elements into the CdSe.

14. The laser vibrometer of claim 12, wherein:
the photo-EMF sensor comprises a nanotechnology based bandgap tuned device.

15. The laser vibrometer of claim 12, wherein:
Wherein the reference beam is shifted to a different frequency than that of the sensing beam.

16. A chemical species detector, comprising:
a light source configured to produce beams of monochromatic light including:
a first beam, having a wavelength corresponding to an absorption feature of the chemical species to be detected;
a second beam; and
a third beam;
a pressure-sensing diaphragm which when impacted by the pressure waves resulting from the first beam interacting with a chemical species that is located away from the third beam responsively vibrates;
a photo-electromotive force (photo-EMF) sensor, configured and arranged to detect displacements of the pressure sensing diaphragm as little as 10 femtometers;
a housing defining an interior space, and
wherein the light source the pressure-sensing diaphragm, the photo-EMF sensor, the second beam and the third beam are contained within the interior space;
wherein the chemical species is located outside of the interior space and the first beam is directed outside of the interior space;
wherein the third beam is directed against the second side of the pressure sensing diaphragm; and
wherein the third beam is directed to the photo-EMF sensor from the pressure-sensing diaphragm which photo-EMF sensor outputs a signal corresponding to the displacement of the diaphragm caused by the incident pressure wave; and
wherein the second beam is frequency shifted from that of the third beam and the sensor is configured to perform phase measurements by heterodyning a frequency shifted second beam and the third beam.

* * * * *